United States Patent
Matsuda et al.

(10) Patent No.: US 8,367,076 B2
(45) Date of Patent: Feb. 5, 2013

(54) **GLYCEROGLYCOLIPID ANTIGEN OF *MYCOPLASMA PNEUMONIAE***

(75) Inventors: Kazuhiro Matsuda, Tokyo (JP); Yuko Shingu, Tokyo (JP)

(73) Assignee: M Bio Technology Inc., Tokyo (JP)

( * ) Notice: Subject to any disclaimer, the term of this patent is extended or adjusted under 35 U.S.C. 154(b) by 678 days.

(21) Appl. No.: 12/304,550

(22) PCT Filed: Jun. 13, 2007

(86) PCT No.: PCT/JP2007/062358
§ 371 (c)(1),
(2), (4) Date: Feb. 13, 2009

(87) PCT Pub. No.: WO2007/145362
PCT Pub. Date: Dec. 21, 2007

(65) Prior Publication Data
US 2009/0263823 A1  Oct. 22, 2009

(30) Foreign Application Priority Data

Jun. 14, 2006 (JP) ................................. 2006-164722

(51) Int. Cl.
*A61K 39/02* (2006.01)
(52) U.S. Cl. ................. 424/264.1; 424/234.1; 424/184.1
(58) Field of Classification Search .................. None
See application file for complete search history.

(56) References Cited

FOREIGN PATENT DOCUMENTS
JP  2005-110545 A   4/2005
JP  2006-117582 A   5/2006

OTHER PUBLICATIONS

Chandler et al (Infection and Immunity, 57(4):1131-1136, 1989).*
Arakawa et al., "Immunoadsorption therapy for a child with Guillian-Barre syndrome subsequent to Mycoplasma infection: a case study," Brain & Development, 2005, 27:431-433.
Braun et al., "*Mycoplasma pneumoniae*: usual suspect and unsecured diagnosis in the acute setting," The Journal of Emergency Medicine, 2006, 30(4):371-375.
Hirai et al., "Application of an Indirect Innumofluorescence Test for Detection of *Mycoplasma pneumonia* in Respiratory Exudates," Journal of Clinical Microbiology, Sep. 1991, 29(9):2007-2012.
Kojima et al., "Seasonal changes in glycolipids and phospholipids of *Pinus nigra* needles," Research Bulletin of Obihiro University of Agriculture and Veterinary Medicine, 1990, 17:13-19, with English summary on p. 19.
Kojima et al., "Structure of novel glyceroglycolipids in Adzuki bean (*Vigna angularis*) seeds," Biochem. Cell. Biol., 1990, 68(1):59-64.
Kojima et al., "Two Digalactosyldiacylglycerols with Different Anomeric Configuration in Leguminous Seeds," J. Sci. Food Agric., 1991, 54(1):35-41.
Miyachi et al., "Synthesis of Cell-membrane Glyceroglycolipids from *Mycoplasma pneumoniae*," The Japanese Society of Carbohydrate Research Nenkai Yoshishu, Jul. 2007, p. 151, p. 2-29, with English summary.
Shingu et al., "Syntheses and Biological Activities of Novel Glycosyl-sn-glyceride, Species-Specific Immunodeterminants of Mycoplasma Fermentans," The Japanese Society of Carbohydrate Research Nenkai Yoshishu, 2003, p. 35, with English summary.
Yang et al., "Cytokines in *Mycoplasma pneumoniae* infections," Cytokine & Growth Factor Reviews, 2004, 15:157-168.
Supplementary European Search Report dated May 25, 2010, in corresponding EP 07745525.1, 9 pages.
Guella et al., "A new solution for an old problem: the regiochemical distribution of the acyl chains in galactolipids can be established by electrospray ionization tandem mass spectrometry," Rapid Communications in Mass Spectrometry, 2003, 17:1982-1994.
Yamauchi et al., "Analysis of Molecular Species of Glycolipids in Fruit Pastes of Red Bell Pepper (*Capsicum annuum* L.) by High-Performance Liquid Chromatography-Mass Spectrometry," J. Agric. Food Chem., 2001, 49:622-627.

* cited by examiner

*Primary Examiner* — Patricia A Duffy

(57) ABSTRACT

The present invention provides a novel glyceroglycolipid produced by *Mycoplasma pneumoniae*. The glyceroglycolipid can be used as a diagnostic marker for a disease caused by *Mycoplasma pneumoniae*.

8 Claims, 8 Drawing Sheets

3-O-[(β-D-Galactopyranosyl)-(1,6)-(β-D-galactopyranosyl)]-1,2-di-O-acyl-sn-glycerol (1)

3-O-[(β-D-Glucopyranosyl)-(1,6)-(β-D-galactopyranosyl)]-1,2-di-O-acyl-sn-glycerol (2)

1. extracted lipids
2. first purification: eluted with C:M=9:1
3.     C:M=8:2
4.     C:M=7:3
5.     C:M=6:4
6.     C:M=5:5
7.     C:M=4:6
8.     C:M=3:7
9.     C:M=2:8
10.     C:M=1:9

11. final sample

GLYCEROGLYCOLIPID ANTIGEN OF *MYCOPLASMA PNEUMONIAE*

CROSS-REFERENCE TO RELATED APPLICATIONS

This application is a National Stage application of PCT/JP2007/062358, filed Jun. 13, 2007, which claims priority from Japanese application JP 2006-164722, filed Jun. 14, 2006.

TECHNICAL FIELD

The present invention relates to a glyceroglycolipid antigen substance, which has a novel structure isolated from *Mycoplasma pneumoniae*.

BACKGROUND ART

*Mycoplasma* is the simplest and smallest microbial group, which does not have any cell wall. *Mycoplasma pneumoniae*, which is a kind of *Mycoplasma*, is a microorganism causing mycoplasma pneumonia. It is difficult, particularly in children, to distinguish mycoplasma pneumonia from pneumonia caused by *Streptococcus pneumoniae* or *Chlamydia pneumoniae*, and effective antibiotics to *Mycoplasma pneumoniae* are different from those of them. It is not uncommon to miss the diagnosis and use a wrong antibiotic, leading to serious symptoms. It is desired to accurately judge infection and diagnose a disease.

However, the existing *Mycoplasma pneumoniae* detection method, which utilizes a *Mycoplasma pneumoniae* extract mixture as an antigen, has the problems that specificity is low, and that reproducibility cannot be maintained due to the difference between lots of extract.

It has been reported that *Mycoplasma pneumoniae* is a substance responsible for mycoplasma pneumonia, asthma and nervous diseases. However, the pathogenic mechanism of them has not been clarified yet (Japanese Laid-Open Patent Publication No. 2005-110545; The Journal of Emergency Medicine, 2006, 30, 4, 371-375; Cytokine & Growth Factor Reviews, 2004, 15, 2-3, 157-168; and Brain and Development, 2005, 27, 6, 431-433).

DISCLOSURE OF THE INVENTION

Under the above-described circumstances, it is desired that a method for accurately judging *Mycoplasma pneumoniae* infection and a method for accurately diagnosing a disease related to the microorganism are established. In particular, a highly specific *Mycoplasma pneumoniae* detection method is desired.

In order to clarify pathogenicity of *Mycoplasma pneumoniae*, the present inventors isolated glycolipids having antigenecity from membrane lipid fractions of *Mycoplasma pneumoniae*, purified them, and attempted to conduct structural analysis thereof. As a result, a novel glycolipid, which may have important physiological activity, was successfully isolated, and its absolute structure was determined. Further, it was confirmed that an antibody to the glycolipid antigen of the present invention is found in a patient suffering from a nervous disease.

Therefore, the present invention provides: the following compound (the glyceroglycolipid of the present invention); a composition, a diagnostic agent or a kit comprising the compound; and a method for diagnosing a disease caused by *Mycoplasma pneumoniae* using the same:

(1) A compound represented by the following general formula:

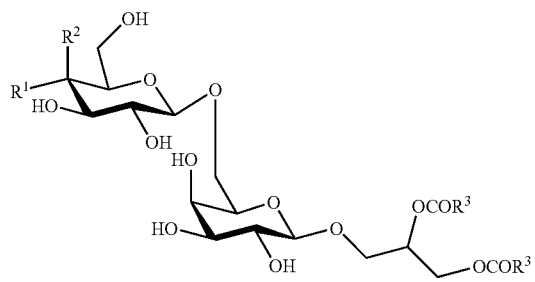

wherein in the formula: when $R^1$=OH, $R^2$=H, and when $R^1$=H, $R^2$=OH; and each $R^3$ can be independently selected from saturated or unsaturated hydrocarbon groups, or salts thereof.

(2) The compound according to item (1), wherein $R^3$ is —$(CH_2)_nCH_3$ (wherein n is 12, 14, 16 or 18).

(3) The compound according to item (1), which is any one of the following compounds:
3-O-[(β-D-galactopyranosyl)-(1,6)-(β-D-galactopyranosyl)]-1,2-di-O-acyl-sn-glycerol;
3-O-[(β-D-glucopyranosyl)-(1,6)-(β-D-galactopyranosyl)]-1,2-di-O-acyl-sn-glycerol;
and salts thereof.

(4) A composition comprising the compound according to any one of items (1) to (3).

(5) A diagnostic agent for a disease caused by *Mycoplasma pneumoniae*, which comprises the compound according to any one of items (1) to (3).

(6) The diagnostic agent according to item (5), wherein the disease is mycoplasma pneumonia, asthma or a nervous disease.

(7) A diagnostic kit for a disease caused by *Mycoplasma pneumoniae*, which comprises the compound according to any one of items (1) to (3) or the composition according to item (4).

(8) The diagnostic kit according to item (7), wherein the disease is mycoplasma pneumonia, asthma or a nervous disease.

(9) A method for diagnosing a disease caused by *Mycoplasma pneumoniae*, comprising the steps of:
bringing the compound according to any one of items (1) to (3) or the composition according to item (4) into contact with a sample from a subject; and
immunologically detecting or measuring an antibody to the compound according to any one of items (1) to (3) in the sample.

(10) The diagnostic method according to item (9), wherein the disease is mycoplasma pneumonia, asthma or a nervous disease.

(11) The diagnostic agent, diagnostic kit or diagnostic method according to any one of items (5) to (10), utilizing the compound according to any one of items (1) to (3), which has galactose at the nonreducing terminus.

(12) The diagnostic agent, diagnostic kit or diagnostic method according to any one of items (5) to (10), utilizing the compound according to any one of items (1) to (3), which has glucose at the nonreducing terminus.

(13) An antibody to a compound represented by the following general formula:

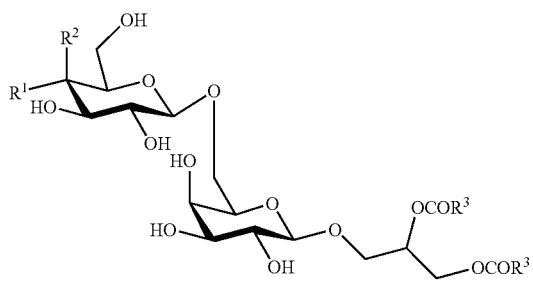

wherein in the formula: when $R^1$=OH, $R^2$=H, and when $R^1$=H, $R^2$=OH; and each $R^3$ can be independently selected from saturated or unsaturated hydrocarbon groups, or salts thereof.

(14) The antibody according to item (13), wherein $R^3$ is —$(CH_2)_n CH_3$ (wherein n is 12, 14, 16 or 18).

(15) The antibody according to item (13), which is an antibody to any one of the following compounds:
3-O-[(β-D-galactopyranosyl)-(1,6)-(β-D-galactopyranosyl)]-1,2-di-O-acyl-sn-glycerol;
3-O-[(β-D-glucopyranosyl)-(1,6)-(β-D-galactopyranosyl)]-1,2-di-O-acyl-sn-glycerol;
and salts thereof.

(16) The antibody according to any one of items (13) to (15), which is a monoclonal antibody.

(17) A composition comprising the antibody according to any one of items (13) to (16).

(18) A diagnostic agent for a disease caused by *Mycoplasma pneumoniae*, which comprises the antibody according to any one of items (13) to (16).

(19) The diagnostic agent according to item (18), wherein the disease is mycoplasma pneumonia, asthma or a nervous disease.

(20) A kit for detecting *Mycoplasma pneumoniae*, which comprises the antibody according to any one of items (13) to (16) or the composition according to item (17).

(21) A kit for diagnosing a disease caused by *Mycoplasma pneumoniae*, which comprises the antibody according to any one of items (13) to (16) or the composition according to item (17).

(22) The kit according to item (21), wherein the disease is mycoplasma pneumonia, asthma or a nervous disease.

(23) A method for detecting the presence of *Mycoplasma pneumoniae*, comprising the steps of:
bringing the antibody according to any one of items (13) to (16) or the composition according to item (17) into contact with a sample; and
immunologically detecting or measuring binding between an antigen substance in the sample and the antibody according to any one of items (13) to (16).

(24) A method for diagnosing a disease caused by *Mycoplasma pneumoniae*, comprising the steps of:
bringing the antibody according to any one of items (13) to (16) or the composition according to item (17) into contact with a sample from a subject; and
immunologically detecting or measuring binding between an antigen substance in the sample and the antibody according to any one of items (13) to (16).

(25) The method according to item (24), wherein the disease is mycoplasma pneumonia, asthma or a nervous disease.

The present invention also provides the following methods for producing a diagnostic agent for a disease caused by *Mycoplasma pneumoniae*:

(25) A method for producing a diagnostic agent for a disease caused by *Mycoplasma pneumoniae*, comprising the step of binding the compound according to any one of items (1) to (3) or the composition according to item (4) to a suitable support or carrier.

(26) The method according to item (25), wherein the disease is mycoplasma pneumonia, asthma or a nervous disease.

(27) A method for producing a diagnostic agent for a disease caused by *Mycoplasma pneumoniae*, comprising the step of binding the antibody according to any one of items (13) to (16) or the composition according to item (16) to a suitable support or carrier.

(28) The method according to item (27), wherein the disease is mycoplasma pneumonia, asthma or a nervous disease.

Since the glyceroglycolipid of the present invention is the main antigen of *Mycoplasma pneumoniae*, it may be a molecular basis for highly-sensitively and accurately detecting *Mycoplasma pneumoniae*. Therefore, by utilizing the glycolipid, an accurate diagnostic method, a diagnostic agent and a diagnostic kit for a disease caused by *Mycoplasma pneumoniae* can be developed.

| | |
|---|---|
| 1 | adhesive sheet |
| 2 | impregnation member |
| 3 | membrane carrier |
| 31 | capture site |
| 4 | absorption member |
| 5 | sample addition member |

Figure 9:
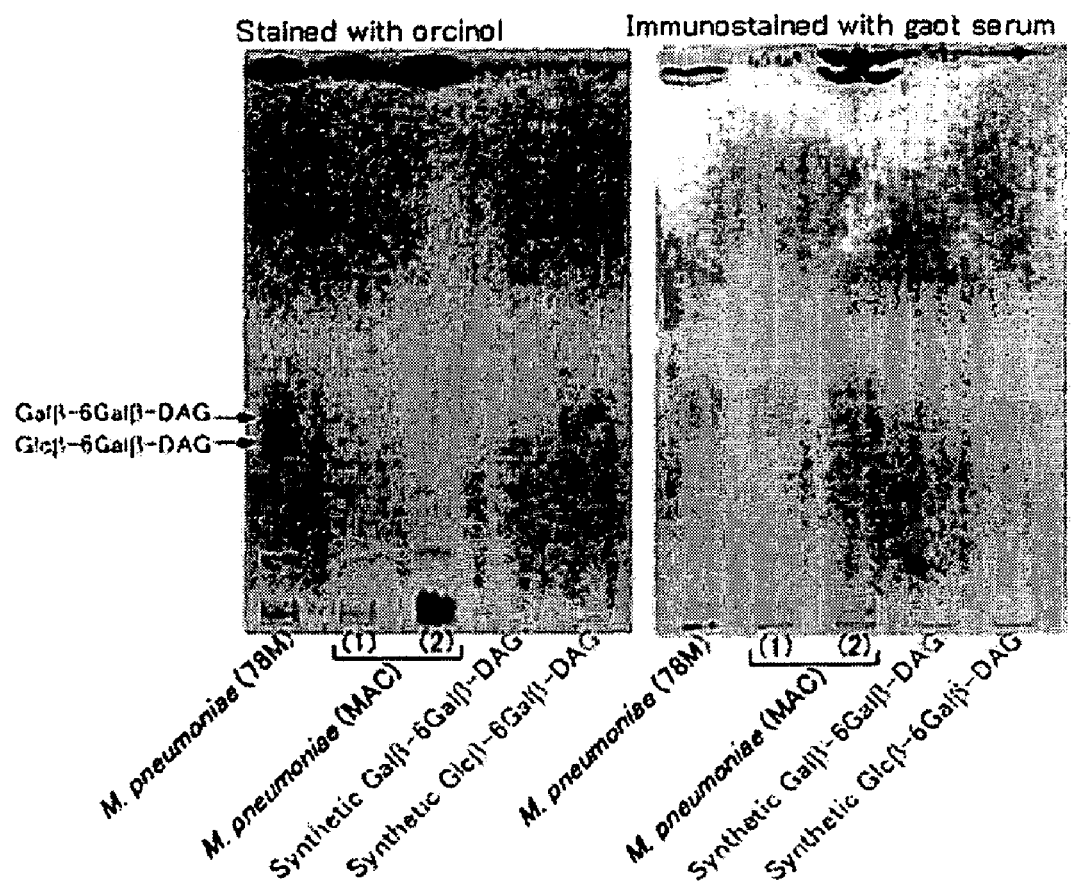

FIG. 9 is a photograph showing results obtained by developing a lipid mixture extracted from a body of *Mycoplasma pneumoniae*, and Galβ1-6Galβ-3DAG and Glcβ1-6Galβ-3DAG, which were prepared by means of chemical synthesis, on a HTLC plate and reacting them with goat serum. The right figure shows a result obtained by immunostaining using the obtained goat serum. The left figure shows a result obtained by subjecting the HTLC plate on which the compounds were developed to orcinol staining.

Figure 10:
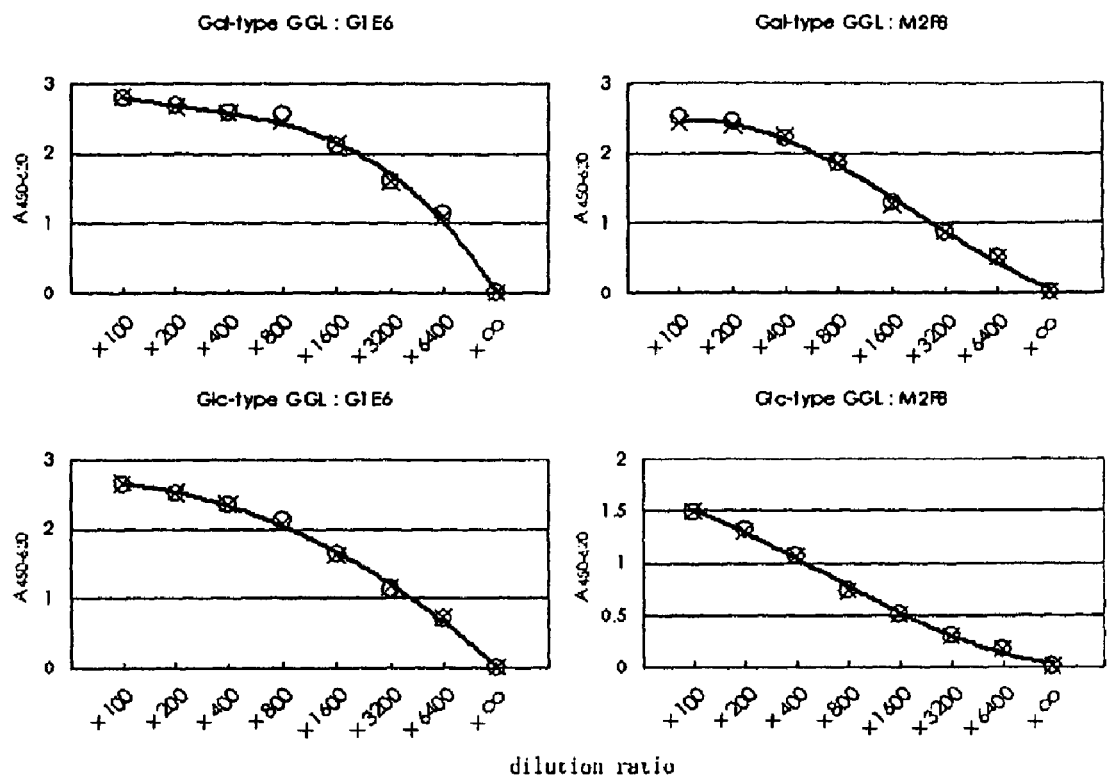

FIG. 10 shows results of ELISA showing reactivity of each of Galβ1-6Galβ-3DAG and Glcβ1-6Galβ-3DAG with an antigen and a monoclonal antibody purified by ammonium sulfate fraction. The monoclonal antibody reacted with both GalGL and GulGL.

BEST MODE FOR CARRYING OUT THE INVENTION

The present inventors successfully isolated/purified the main compound whose antigenecity is particularly high from antigen substances of *Mycoplasma pneumoniae*. Further, the compound was subjected to structural analysis and a novel glyceroglycolipid was identified.

1. Glyceroglycolipid of the Present Invention

In one embodiment, the present invention provides a glyceroglycolipid, which is newly isolated from antigen substances of *Mycoplasma pneumoniae*, and whose structure is determined.

The glyceroglycolipid provided by the present invention is a glyceroglycolipid produced by *Mycoplasma pneumoniae*, which is represented by the following structural formula:

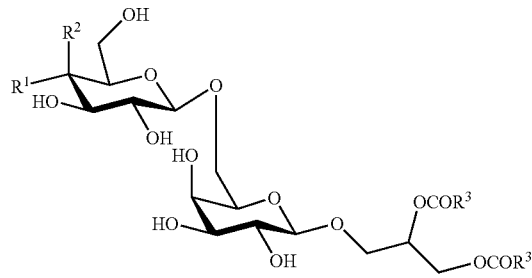

wherein in the formula, when $R^1$=OH, $R^2$=H, and when $R^1$=H, $R^2$=OH; and each $R^3$ can be independently selected from saturated or unsaturated hydrocarbon groups, or salts thereof. Preferably, $R^3$ is a saturated hydrocarbon represented by —$(CH_2)_nCH_3$ (wherein n is 12, 14, 16 or 18).

Particularly preferably, the glyceroglycolipid provided by the present invention is a glyceroglycolipid represented by the following structural formula:

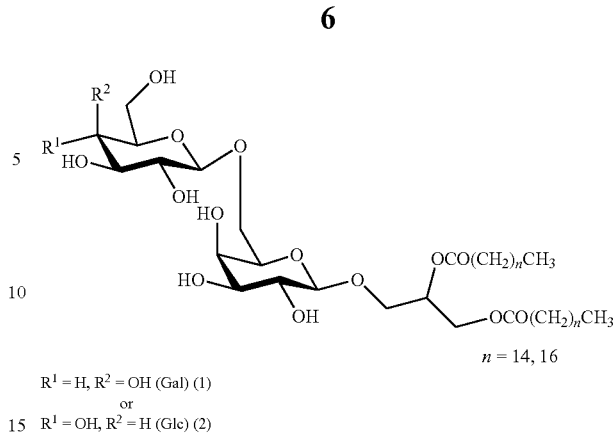

$n = 14, 16$ $R^1$ = H, $R^2$ = OH (Gal) (1)
or
$R^1$ = OH, $R^2$ = H (Glc) (2)

or salts thereof.

Regarding the above-described structural formula, in the case of (1), it is 3-O-[(β-D-Galactopyranosyl)-(1,6)-(β-D-galactopyranosyl)]-1,2-di-O-acyl-sn-glycerol (hereinafter sometimes abbreviated as "Galβ-6Galβ-3DAG"), and in the case of (2), it is 3-O-[(β-D-Glucopyranosyl)-(1,6)-(β-D-galactopyranosyl)]-1,2-di-O-acyl-sn-glycerol (hereinafter sometimes abbreviated as "Glcβ-6Galβ-3DAG"). The acyl group is a palmitoryl group or stearoyl group.

As used herein, the term "glyceroglycolipid of the present invention" refers to a glyceroglycolipid represented by the above structural formula and salts thereof. Examples of salts include those with a physiologically acceptable acid (e.g., inorganic acid, organic acid) or base (e.g., alkali metal salt), and physiologically acceptable acid addition salts are particularly preferable. Examples of such salts include salts with an inorganic acid (e.g., hydrochloric acid, phosphoric acid, hydrobromic acid and sulfuric acid) and salts with an organic acid (e.g., acetic acid, formic acid, propionic acid, fumaric acid, maleic acid, succinic acid, tartaric acid, citric acid, malic acid, oxalic acid, benzoic acid, methanesulfonic acid, and benzenesulfonic acid).

The glyceroglycolipid of the present invention is a glycolipid produced by *Mycoplasma pneumoniae*, and is useful as a marker for detecting *Mycoplasma pneumoniae* or diagnosing a disease caused by *Mycoplasma pneumoniae*. For example, when using an antibody which specifically binds to the glyceroglycolipid of the present invention, the detection of *Mycoplasma pneumoniae* or the diagnosis of a disease caused by *Mycoplasma pneumoniae* can be performed using an immunological technique.

2. Method for Diagnosing a Disease Caused by *Mycoplasma pneumoniae* by Detecting an Autoantibody to the Glyceroglycolipid of the Present Invention According to one embodiment of the present invention, a method for diagnosing a disease caused by *Mycoplasma pneumoniae*, which is characterized by the presence of an anti-glyceroglycolipid antibody in a sample from a subject, is provided. This method includes the step of bringing the glyceroglycolipid of the present invention into contact with a sample from a subject.

A method for measuring an anti-glyceroglycolipid antibody to be used in the method of the present invention is not particularly limited as long as it makes it possible to measure an anti-glyceroglycolipid antibody in a sample from a subject. Typical examples thereof include an immunological measurement method based on antigen-antibody reaction. The immunological measurement method to be used in the present invention includes the steps of: bringing the glyceroglycolipid of the present invention into contact with a sample from a subject; and detecting the presence of an immune complex of the glyceroglycolipid of the present invention and an anti-glyceroglycolipid antibody in the sample from the subject.

As used herein, the term "disease caused by *Mycoplasma pneumoniae*" refers to a disease caused by *Mycoplasma pneumoniae* infection. Typically, the disease caused by *Mycoplasma pneumoniae* is characterized in that the glyceroglycolipid of the present invention or a salt thereof, or an autoantibody to the glyceroglycolipid of the present invention is detected in a biological sample from a patient suffering from the disease. Examples of the diseases caused by *Mycoplasma pneumoniae* include, but are not limited to, mycoplasma pneumonia, asthma and a nervous disease.

As used herein, the term "subject" refers to a mammal which may be infected with *Mycoplasma pneumoniae* (e.g., human, monkey, cow, horse, sheep, rabbit, rat, mouse, etc.), preferably a human, and most preferably a human infected with *Mycoplasma pneumoniae*, a human who may be affected with a disease caused by *Mycoplasma pneumoniae*, or a human affected with a disease caused by *Mycoplasma pneumoniae*.

As used herein, the term "sample" or "biological sample" includes body fluid (e.g., whole blood, plasma, serum, joint fluid, spinal fluid, saliva, amniotic fluid, urine, sweat, pancreatic fluid, and synovial fluid), tissue, cell and the like collected from a subject.

In the method of the present invention for diagnosing and prognosing a disease caused by *Mycoplasma pneumoniae* based on the detection of an autoantibody in a sample from a subject, the disease is confirmed using biological samples from a subject suffering from the disease and a control not suffering from the disease. A biological sample such as serum which may contain an autoantibody can be obtained from a subject who may have a specific disease or a subject who may have a predisposition to the disease. Body fluid of the same kind is obtained from a control not suffering from the disease.

According to the present invention, the measurement of an autoantibody responsive to the glyceroglycolipid antigen of the present invention can be used for initial diagnosis of diseases such as mycoplasma pneumonia. Moreover, monitoring of autoantibody levels can be used for prognostically clarifying the progression of a disease.

3. Method for Measuring Anti-Glyceroglycolipid Antibody

Detection of an autoantibody to the glyceroglycolipid of the present invention in a sample (e.g., a serum sample from a subject) can be performed using any of various methods. Examples of such methods include immunoassay, and examples thereof include, but are not limited to, western blotting, radioimmunoassay, ELISA (solid-phase enzyme immunoassay), "sandwich" immunoassay, immunoprecipitation assay, precipitin reaction, gel diffusion precipitin reaction, immunodiffusion assay, aggregation assay, complement fixation assay, immunoradiometric assay, fluorescent immunoassay, protein A immunoassay, etc.

Such immunoassays are performed using a method, in which a sample from a subject is brought into contact with the glyceroglycolipid antigen of the present invention or a composition comprising the antigen under conditions in which a specific antigen-antibody binding occurs, and an immunospecific binding of an autoantibody is detected or the amount thereof is measured. In a specific embodiment, such binding of an autoantibody using a tissue section can be utilized, for example, in order to detect the presence of autoantibody. In this case, when an autoantibody is detected, it indicates the presence of disease. The level of the autoantibody in a serum sample is compared to the level of that from a subject who does not have a disease present in a serum sample of the same kind.

Immunoassays can be performed using various methods. One example of such methods for performing an immunoassay includes anchoring the glyceroglycolipid of the present invention onto a solid support and detecting an anti-glyceroglycolipid antibody which specifically binds to the glyceroglycolipid.

More specifically, the method for measuring an anti-glyceroglycolipid antibody in a sample comprises, for example, the following steps of:

(1) reacting an anti-glyceroglycolipid antibody in a biological sample with the glyceroglycolipid of the present invention immobilized on a solid phase to form an immune complex (primary reaction);

(2) reacting the immune complex produced in step (1) with a labeled anti-human immunoglobulin antibody to form an immune complex (secondary reaction);

(3) separating a labeled anti-human immunoglobulin antibody which does not form any immune complex from the solid phase;

(4) measuring the amount or activity of the label in the immune complex produced in the solid phase; and (5) comparing a measurement value obtained in the measurement in (4) with the analytical curve produced using the anti-glyceroglycolipid antibody at a already-known concentration in advance.

According to need, the step of washing the solid phase after the primary reaction can be added between the step (1) and the step (2). The steps (1) and (2) can be carried out simultaneously. In the measurement of the anti-glyceroglycolipid antibody in the biological sample of the present invention, it can be reacted with a biotinylated anti-human immunoglobulin antibody in the secondary reaction. In this case, an immune complex produced by the secondary reaction (a complex comprising the glyceroglycolipid of the present invention, the anti-glyceroglycolipid antibody and the biotinylated anti-human immunoglobulin antibody) can be reacted with a (strept)avidin-labeled antibody, and the amount of avidin-labeled antibody in the produced immune complex is measured. In the secondary reaction, a (labeled) aptamer which reacts with the anti-glyceroglycolipid antibody can be used instead of a (labeled) anti-human immunoglobulin antibody.

The primary reaction can be performed in an aqueous medium (e.g., a liquid phase in wells) or a dry medium (e.g., a solid phase support). Examples of solid phases to which the glyceroglycolipid of the present invention is immobilized include: a polystyrene plate such as a microtiter plate; granular products (beads) made of glass or a synthetic resin; a spherical product (ball) made of glass or a synthetic resin; latex; magnetic particles; various membranes such as nitrocellulose membrane; a test tube made of a synthetic resin; and a silica gel plate. The secondary reaction can also be performed in an aqueous medium or a dry medium. Examples of methods for measuring the amount or activity of the label in the immune complex produced on the solid phase by the secondary reaction include an optical density method (calorimetric method), a fluorescence method, an emission method, and a radio-active method. When the label is an enzyme, a substrate for the enzyme is reacted with the enzyme, a substance produced is measured, and thereby the enzyme activity in the immune complex can be measured. The reaction between the substrate and the enzyme is preferably performed in an aqueous medium.

A subject, who is judged as infected with *Mycoplasma pneumoniae* or diagnosed as having a disease caused by

*Mycoplasma pneumoniae* according to the above-described method, can undergo suitable treatment or therapy.

4. Composition, Diagnostic Agent and Diagnostic Kit Comprising the Glyceroglycolipid of the Present Invention In one embodiment, the present invention provides a composition comprising the glyceroglycolipid of the present invention. In another embodiment, the present invention provides a diagnostic agent for a disease caused by *Mycoplasma pneumoniae*, which comprises the glyceroglycolipid of the present invention. In yet another embodiment, the present invention provides a diagnostic kit for a disease caused by *Mycoplasma pneumoniae*, which comprises the glyceroglycolipid of the present invention or the above-described composition of the present invention.

The composition comprising the glyceroglycolipid of the present invention may comprise a suitable carrier, excipient, buffering agent, diluent, etc. The composition of the present invention can be used, for example, to be administered to animals such as mouse, rat, rabbit, etc. in order to prepare an antibody to the glyceroglycolipid of the present invention. Alternatively, the composition of the present invention can be used in order to detect an antibody to the glyceroglycolipid of the present invention in a sample (e.g., anti-Galβ-6Galβ-3DAG antibody or anti-Glcβ-6Galβ-3DAG antibody). Alternatively, the composition of the present invention can be used as a diagnostic agent for a disease caused by *Mycoplasma pneumoniae*. Moreover, the composition of the present invention may be contained in a diagnostic kit for a disease caused by *Mycoplasma pneumoniae*.

The diagnostic agent and kit of the present invention comprising the glyceroglycolipid of the present invention can be used according to the above-described method for measuring the anti-glyceroglycolipid antibody. The kit of the present invention may further comprise an anti-human immunoglobulin antibody, etc. labeled with biotin, etc. for the above-described secondary reaction. In the kit of the present invention, the glyceroglycolipid of the present invention may be immobilized to a solid phase support such as: a polystyrene plate such as a microtiter plate; granular products (beads) made of glass or a synthetic resin; a spherical product (ball) made of glass or a synthetic resin; latex; magnetic particles; various membranes such as nitrocellulose membrane; a test tube made of a synthetic resin; and a silica gel plate. The kit of the present invention may also comprise a buffer solution, etc. to be used as a liquid phase for performing reaction. The kit of the present invention may also comprise an instruction, etc. made by the manufacturer.

In one embodiment, the present invention also provides a method for producing a diagnostic agent for a disease caused by *Mycoplasma pneumoniae*, which comprises the step of combining the glyceroglycolipid of the present invention or the composition comprising the glyceroglycolipid of the present invention with a suitable support or a carrier. Examples of carriers include insoluble polysaccharides such as agarose, dextran and cellulose, synthetic resins such as polystyrene, polyacrylamide and silicon, and glass.

5. Antibody to the Glyceroglycolipid of the Present Invention and Use Thereof

In one embodiment, the present invention provides an antibody which specifically binds to the glyceroglycolipid of the present invention. The antibody of the present invention has reaction specificity to a *Mycoplasma pneumoniae*-specific glyceroglycolipid (glyceroglycolipid of the present invention). Therefore, when using this, the glyceroglycolipid in an analyte can be measured immunologically. The antibody of the present invention can be used for diagnosis of a disease caused by *Mycoplasma pneumoniae*.

(I) Preparation of the Antibody of the Present Invention

The antibody of the present invention can be obtained by: immunizing an animal with the glyceroglycolipid of the present invention derived from *Mycoplasma pneumoniae* as an antigen; and collecting serum from the animal, or collecting an antibody-producing cell of the animal, which is then made permanently culturable, and collecting a product from its culture. Hereinafter, one example of method for preparing the antibody of the present invention is described, but the method of the present invention is not limited thereto. Preparation may be carried out using other methods as long as the glyceroglycolipid of the present invention derived from *Mycoplasma pneumoniae* is used as an antigen.

(1) Preparation of Polyclonal Antibody

For example, monophosphate lipid, Freund's complete adjuvant, and mineral oil are added to a lipid extract from *Mycoplasma pneumoniae* obtained in the way described in the Examples below to be mixed, PBS (phosphate buffered saline) containing 0.1% (v/v) Tween 80 is further added to the mixture, and the obtained mixture is emulsified.

Next, the emulsified product is administered subcutaneously or intraperitoneally to an animal such as mouse, rat, rabbit, guinea pig and sheep. After the first immunization, additional immunization is performed using an ordinary method during the second or third week, and then antiserum having high titer can be obtained. One week after the final immunization, blood is collected and serum is separated therefrom. This serum is subjected to heat treatment to deactivate a complement, and after that, immunogloblin fraction is obtained using a method similar to general antibody preparation methods such as salting-out with ammonium sulfate and ion exchange chromatography. Desirably, after the final immunization, increase in antibody titer in blood is confirmed by means of enzyme immunoassay, etc.

An antibody obtained in the above-described way specifically binds to the glyceroglycolipid from *Mycoplasma pneumoniae*. When the specification describes that an antibody "specifically binds" to an antigen (e.g., glyceroglycolipid of the present invention), it means that the antibody binds to the antigen with a substantially higher affinity compared to those to other substances (e.g., glyceroglycolipids other than that of the present invention). As used herein, the term "substantially higher affinity" means an affinity which is high enough to be distinctly detected from a specific antigen using a desired measurement apparatus. Typically, the binding constant ($K_a$) is at least $10^7 M^{-1}$, preferably at least $10^8 M^{-1}$, more preferably $10^9 M^{-1}$, and even more preferably $10 M^{-1}$, $10^{11} M^{-1}$, $10^{12} M^{-1}$ or higher (e.g., up to $10^{13} M^{-1}$ or higher).

When using the purified glyceroglycolipid of the present invention instead of the lipid extract from *Mycoplasma pneumoniae*, a polyclonal antibody having reaction specificity to the glyceroglycolipid of the present invention can be obtained.

(2) Preparation of Monoclonal Antibody

A monoclonal antibody can be obtained according to the method of Koehler and Milstein (Nature, 495-492, 1975). That is, an antibody-producing cell from a mammal which produces an antibody to glyceroglycolipid is fused with a myeloma cell to prepare hybridoma, a hybridoma which produces an antibody of interest is cloned, and this hybridoma is cultured to obtain a monoclonal antibody in a culture solution. Hereinafter, every step is described in detail.

(i) Immunization of Animal and Preparation of Antibody-Producing Cell

A cell which produces an antibody to glyceroglycolipid can be obtained by immunizing an animal such as mouse, rat, rabbit, guinea pig and sheep with the glyceroglycolipid and preparing spleen cell, lymph node cell, peripheral blood, etc. from the animal. Immunization of the animal with the glyceroglycolipid can be performed in a manner similar to that in item (1) above.

In order to obtain a monoclonal antibody having reaction specificity to the glyceroglycolipid of the present invention, an animal can be immunized with the purified glyceroglycolipid of the present invention. Alternatively, hybridoma is prepared using an antibody-producing cell from an animal immunized with a mixture of glyceroglycolipid, and a line which produces a monoclonal antibody having reaction specificity to the glyceroglycolipid of the present invention is selected from the obtained hybridoma. According to this method, it is not necessary to obtain the glyceroglycolipid of the present invention in an amount required for immunization of animal. It is sufficient to obtain the glyceroglycolipid of the present invention in a slight amount which allows detection by means of enzyme immunization.

(ii) Preparation of Hybridoma

An antibody-producing cell is collected from an animal immunized with the glyceroglycolipid, and the cell is fused with a myeloma cell. As the myeloma cell to be used for cell fusion, cell lines from various mammals can be utilized. However, it is preferred to use a cell line from the same animal as that used in the preparation of the antibody-producing cell. Further, it is preferred to use a myeloma cell line having a marker so that only hybridoma can proliferate (unfused myeloma cells cannot survive) for the purpose of distinguishing between unfused cells and fused cells after cell fusion. For example, an 8-azaguanine resistant line lacks hypoxanthine-guanine-phosphoribosyl transferase (HGPRT), and nucleic acid synthesis depends on the de novo synthetic pathway. In the case of a fused cell (hybridoma) of such a myeloma cell and a normal antibody-producing cell, even if the de novo synthetic pathway is inhibited by aminopterin in a medium containing hypoxanthine, aminopterin and thymidine (HAT medium), since thymidine and hypoxanthine are present, nucleic acid synthesis can be performed via the salvage pathway derived from lymphocytes. It allows proliferation. On the other hand, in the case of an 8-azaguanine resistant myeloma cell, since the de novo synthetic pathway is inhibited by aminopterin, nucleic acid synthesis cannot be performed, leading to cell death. Moreover, an antibody-producing cell as a normal cell cannot be cultured for a long period of time. Therefore, since only the hybridoma produced by cell fusion between the antibody-producing cell and the myeloma cell can proliferate in HAT medium, fused cells can be selected from the group consisting of those and unfused cells (Science, Vol. 145, page 709, 1964). It is preferred to use a line which does not secrete inherent immunoglobulin as a myeloma cell since it makes it easier to obtain an antibody of interest from culture supernatant of hybridoma.

Cell fusion to obtain hybridoma is performed, for example, in the following way. A spleen is taken out from an immunized animal, and it is suspended in RPMI1640 medium to prepare a cell suspension. Spleen cells thereof are mixed with mouse myeloma cells in a logarithmic growth phase such as SP2/0 cells (azaguanine resistant, IgG-nonsecreting: ATCC CRL-1581) so that the ratio between spleen cells and myeloma cells becomes about 10:1 to 1:1. After the mixture is subjected to centrifugal sedimentation, polyethylene glycol having the average molecular weight of 1,000 to 6,000 is added to the sediment so that the final concentration becomes 30 to 50% to cause cell fusion. Cell fusion can be performed by applying electrical pulse to cell mixture instead of adding polyethylene glycol.

After the fusion treatment, the cells are cultured, for example, in RPMI1640 medium containing 10% (v/v) fetal bovine serum (FCS). After that, the cells are suspended in a selection medium such as HAT medium, and subjected to divided injection to a 96-well microtiter plate or the like to perform culture for cultivating only hybridoma.

(iii) Search of Hybridoma which Produces an Antibody Having Reaction Specificity to the Glyceroglycolipid The hybridoma obtained as described above is a mixture of hybridomas which produce various monoclonal antibodies to a plurality of antigens or antigen determination sites. Among them, a line which produces a monoclonal antibody having reaction specificity to the glyceroglycolipid of the present invention (e.g., a monoclonal antibody having reaction specificity to Galβ-6Galβ-3DAG or Glcβ-6Galβ-3DAG) is selected. Further, among monoclonal antibodies which bind to the glyceroglycolipid of the present invention, a line which produces a monoclonal antibody to an antigen determination site having strong antigenecity is preferably selected.

A line which produces monoclonal antibodies to the glyceroglycolipid can be selected by means of enzyme immunization using them as antigens. Examples of such methods include the ELISA method, in which: an antigen is immobilized to a microtiter plate or the like in advance; a hybridoma culture solution is added thereto; a secondary antibody labeled with an enzyme, fluorescent substance, luminescent substance or the like is further added thereto to be incubated; and an antibody is detected by a labeled substance which binds to the antibody. In this regard, alternatively, the antibody can be immobilized, and the antigen and the labeled secondary antibody are sequentially added thereto to be incubated. The ELISA method will be described in detail later.

When the purified glyceroglycolipid of the present invention has not been obtained, lipid fraction of *Mycoplasma pneumoniae* is separated using a plate of high-performance thin-layer chromatography (HPTLC), the culture solution of hybridoma and the labeled secondary antibody are sequentially added to the plate to be incubated, and a position to which the labeled substance binds is detected. If this position is identical to the position where the glyceroglycolipid of the present invention (e.g., Galβ-6Galβ-3DAG or Glcβ-6Galβ-3DAG) is developed by HPTLC, it is recognized that the hybridoma produces a monoclonal antibody to the glyceroglycolipid of the present invention. When the monoclonal antibody to the glyceroglycolipid of the present invention is obtained, by means of affinity chromatography or the like using the same, the glyceroglycolipid of the present invention can be produced by purification of lipid fraction.

When it is confirmed that a hybridoma which produces a monoclonal antibody of interest is contained, cloning is performed by means of limiting dilution or the like utilizing cells in a well in which the hybridoma is contained.

(iv) Preparation of Monoclonal Antibody

When the hybridoma obtained in the above-described way is cultured in a suitable medium, the monoclonal antibody of the present invention can be obtained in the culture supernatant. Moreover, according to the ordinary method, the monoclonal antibody can be purified by means of ammonium sulfate fractionation, ion exchange chromatography, affinity chromatography using protein A or protein G, immunoadsorbent chromatography in which an antigen is immobilized, or the like.

The monoclonal antibody to the glyceroglycolipid of the present invention obtained in this way specifically binds to the glyceroglycolipid of the present invention. Therefore, desirably, this monoclonal antibody does not have cross-reactivity with sialic acid-containing glycolipid (ganglioside), plateletactivating factor (1-alkyl-2-acetylglycero-3-phosphocholine) or a partially deacylated product thereof, phosphatidylcholine or a partially deacylated product thereof, glycolipid such as sphingomyelin and phospholipid, which are present in serum of a healthy human who is not infected with *Mycoplasma pneumoniae*.

The monoclonal antibody of the present invention can be used directly, but a fragment thereof can also be used. At the time of fragmentation of the antibody, it is essential for antigen-antibody binding that the antigen-binding site (Fab) of the antibody is preserved. Therefore, a fragment comprising the antigen-binding site (Fab) obtained by treating the antibody with protease that does not break down the antigen-binding site (e.g., plasmin, pepsin and papain) can be used. Examples of antibody fragments include Fab, $Fab'_2$ and CDR. Further, humanized antibodies, multifunctional antibodies, single-chain antibodies (ScFv), etc. can also be used in the present invention. The class of antibody is not particularly limited, and antibodies having any of isotypes such as IgG, IgM, IgA, IgD and IgE are included. The isotype is preferably IgG or IgM, and more preferably IgG in terms of easiness of purification, etc.

Further, when a nucleotide sequence of a gene encoding the monoclonal antibody of the present invention or an amino acid sequence of the antibody is determined, a fragment comprising an antigen-binding site (Fab) can be prepared using genetic engineering procedure.

6. Composition, Diagnostic Agent and Diagnostic Kit Comprising the Anti-Glyceroglycolipid Antibody of the Present Invention In one embodiment, the present invention provides a composition comprising an antibody to the glyceroglycolipid of the present invention. The composition of the present invention may comprise a suitable carrier, excipient, buffering agent, diluent, etc. Examples of carriers include insoluble polysaccharides such as agarose, dextran and cellulose, synthetic resins such as polystyrene, polyacrylamide and silicon, and glass.

The composition of the present invention can be used in order to detect the glyceroglycolipid of the present invention in a sample. Alternatively, the composition of the present invention can be used to diagnose a disease caused by *Mycoplasma pneumoniae* by detecting the glyceroglycolipid of the present invention in a biological sample.

Therefore, the present invention also provides an agent or kit for diagnosing a disease caused by *Mycoplasma pneumoniae*, which is characterized by the presence of the glyceroglycolipid of the present invention in a sample from a subject. The agent or kit comprises the anti-glyceroglycolipid antibody of the present invention or a composition comprising the antibody.

Therefore, the present invention also provides a method for producing a diagnostic agent for a disease caused by *Mycoplasma pneumoniae*, which comprises the step of combining the antibody of the present invention or a composition comprising the antibody of the present invention with a suitable support or carrier.

The kit of the present invention is used according to the immunoassay method. According to need, at the time of detecting the glyceroglycolipid or *Mycoplasma pneumoniae* in a subject by means of an immunological method, the kit of the present invention may comprise an antibody having reaction specificity to the glyceroglycolipid of the present invention and a secondary antibody in which an antibody to immunoglobulin of an immunized animal other than that used in preparation of the former antibody is labeled with a labeling substance.

One specific example of the kit is that consisting of: a microtiter plate; a blocking agent such as BSA (bovine serum albumin); the glyceroglycolipid of the present invention (standard substance); the antibody of the present invention; a peroxidase-labeled anti-mouse IgG antibody; a hydrogen peroxide solution; OPD; and a buffer solution for washing. Antibodies, glyceroglycolipid of *Mycoplasma pneumoniae* and the like are preferably in the form of freeze-dried product, or dissolved in a solvent in which they are stably preserved. The kit of the present invention may also comprise an instruction made by the manufacturer.

(Measurement Method)

Examples of immunological measurement methods to be used in the present invention include general immunological methods using an antibody such as ELISA method and immunostaining method. For example, the glyceroglycolipid in an analyte solution can be measured in the following way: the analyte solution is brought into contact with a solid phase to which the anti-glyceroglycolipid antibody is bound in order to combine the glyceroglycolipid contained in the analyte solution with the antibody, and non-adsorbed components are separated/removed from the solid phase; subsequently, the glyceroglycolipid of *Mycoplasma pneumoniae* labeled with a labeling substance is brought into contact with the solid phase, and glyceroglycolipid contained in the analyte solution and labeled glyceroglycolipid are subjected to competition reaction; and either of the labeling substance which binds to the solid phase and the labeling substance which does not bind to the solid phase is detected.

Moreover, the glyceroglycolipid in an analyte can be measured in the following way: the analyte solution and the glyceroglycolipid labeled with a labeling substance are brought into contact with a solid phase to which the anti-glyceroglycolipid antibody is bound; glyceroglycolipid contained in the analyte solution and labeled glyceroglycolipid are competitively reacted with the antibody; and either of the labeling substance which binds to the solid phase and the labeling substance which does not bind to the solid phase is detected. Alternatively, a non-labeled standard glyceroglycolipid can be used instead of the labeled glyceroglycolipid, and after the glyceroglycolipid in the analyte and the standard glyceroglycolipid are subjected to competition reaction, the anti-glyceroglycolipid antibody labeled with the labeling substance is brought into contact with the solid phase, and either of the labeling substance which binds to the solid phase and the labeling substance which does not bind to the solid phase can be detected. Also in this case, a labeled secondary antibody can also be used.

Alternatively, the glyceroglycolipid in the analyte solution is combined with the solid phase, and the labeled anti-glyceroglycolipid antibody is brought into contact therewith, and either of the labeling substance which binds to the solid phase and the labeling substance which does not bind to the solid phase is detected.

Various other embodiments of immunological measurement methods are known, and any of such methods can be applied to the present invention. Moreover, other than the above-described methods using the solid phase, methods used in immunoassay of haptens and antigens, e.g., a liquid phase method, in which the glyceroglycolipid in an analyte and labeled glyceroglycolipid are competitively reacted with the antibody; antigen bound to the antibody and free antigen are separated from each other using polyethylene glycol, dextran, a secondary antibody or the like; and a labeling substance of free labeled antigen is detected, can be employed.

Examples of the above-described solid phase include common materials and forms such as agarose beads, latex particles, wells of microtiter plates made of polystyrene, nylon or the like, etc. (particles, fine particles, test tube, microtiter plate, strip, etc.). After combining the solid phase with the antibody or the glyceroglycolipid, blocking is preferably performed using BSA (bovine serum albumin), gelatin or the like. Examples of the labeling substance include: enzymes which can provide color development caused by enzyme reaction such as peroxidase and alkaline phosphatase; radioactive isotopes; and fluorescent dyes such as fluorescein isothiocyanate.

With respect to dyes, 4-chloro-1-naphthol, O-phenylenediamine (OPD), 3,3'-diaminobenzidine or the like is used for peroxidase, and p-nitrophenyl phosphate or the like is used for alkaline phosphatase.

Since the glyceroglycolipid of the present invention is *Mycoplasma pneumoniae*-specific, when the glyceroglycolipid in an analyte is measured using the aforementioned method and the presence/absence or the abundance of the glyceroglycolipid is associated with the presence/absence or the abundance of *Mycoplasma pneumoniae* in the analyte, *Mycoplasma* pneumoniae can be detected.

In the above-described measurement method for the glyceroglycolipid or the detection method for *Mycoplasma pneumoniae*, blood, serum, plasma, cerebral spinal fluid, urine, joint fluid, cell culture medium (supernatant) or the like can be used as an analyte.

Other than the above-described method, *Mycoplasma pneumoniae* can also be detected in the following way: living tissue or cell is directly used, or subjected to a treatment to immobilize the glyceroglycolipid thereto; after that, it is reacted with the anti-glyceroglycolipid antibody labeled with a labeling substance; the labeled antibody is combined with the living tissue or cell infected with *Mycoplasma pneumoniae*; and the labeling substance is measured. Examples of immobilization methods include those using formalin, glutaraldehyde, paraformaldehyde, etc. Alternatively, the labeling substance can be measured in the following way: instead of the anti-glyceroglycolipid antibody labeled with the labeling substance, a non-labeled anti-glyceroglycolipid antibody is reacted with living tissue or cell which is subjected to the immobilization treatment in advance; simultaneously or after that, a secondary antibody in which an antibody to immunoglobulin of an immunized animal other than that used in preparation of the former antibody is labeled with the labeling substance is subjected to reaction; and living tissue or cell infected with *Mycoplasma pneumoniae* is combined with the labeled secondary antibody.

At the time of immunologically measuring glyceroglycolipid in a sample using the antibody of the present invention, for example, when using an antibody which has reaction specificity to both Galβ-6Galβ-3DAG and Glcβ-6Galβ-3DAG, both of them can be measured, and when using an antibody which has reaction specificity to Galβ-6Galβ-3DAG or Glcβ-6Galβ-3DAG, Galβ-6Galβ-3DAG or Glcβ-6Galβ-3DAG can be selectively measured. At the time of measuring Galβ-6Galβ-3DAG or Glcβ-6Galβ-3DAG Galβ-6Galβ-3DAG or Glcβ-6Galβ-3DAG obtained in the way described in the Examples can be used as a labeling substance.

Hereinafter, the present invention will be specifically described by way of illustrative examples, but the present invention is not limited thereto.

EXAMPLES

Example 1

1. Separation and Purification of Glycolipid

*Mycoplasma pneumoniae* (Mac strain) was cultured in PPLO medium in the following way. *Mycoplasma pneumoniae* was cultured at 37° C. in a liquid medium obtained by adding 10% bovine serum, 10% penicillin, 0.0002% phenol red and 1% glucose to PPLO liquid basal medium (manufactured by Difco). Growth of the microorganism was confirmed by pH change of the medium, and after that, centrifugation was performed (16,000×g, 1 hour). This operation was repeated once to provide a sample for lipid extraction. To 200 L (volume in wet condition) of the microorganism sample, a mixed solvent of chloroform and methanol was added to extract lipid fraction.

2. Extraction of Lipid

The sample was suspended in methanol and it was allowed to stand for 4 hours. The double amount of chloroform was added thereto, the fungus body was crushed by ultrasonic wave, and the mixture was left for another 4 hours. Centrifugation was performed (3000 rpm), and supernatant was collected and concentrated to provide a lipid fraction sample.

This lipid sample was subjected to separation and purification by means of column chromatography (filled with silica gel) using chloroform and methanol. In the first stage, solvents, which have the mixing ratio of chloroform:methanol of 9:1, 8:2, 7:3, 6:4, 5:5, 4:6, 3:7, 2:8, 1:9 or 0:10, respectively, were used to produce 10 types of fractions. In the second and third stages, each of the fractions was further subjected to the same column chromatography to further perform separation. In the first stage, 10 types of fractions, which contained a compound of 33 mg, 79 mg, 2 mg, 5 mg, 2 mg, 4 mg, 4 mg, 2 mg, 6 mg or 0 mg (no compound was collected), respectively, were obtained. In the second stage, one of the fractions (79 mg) was further fractionated to obtain 6 types of fractions. Among them, the second fraction was further fractionated to obtain 6 types of fractions in the third stage. Among the obtained fractions, the fourth fraction contained glycolipids 1 and 2. The yield thereof was 15 mg.

Figure 1:
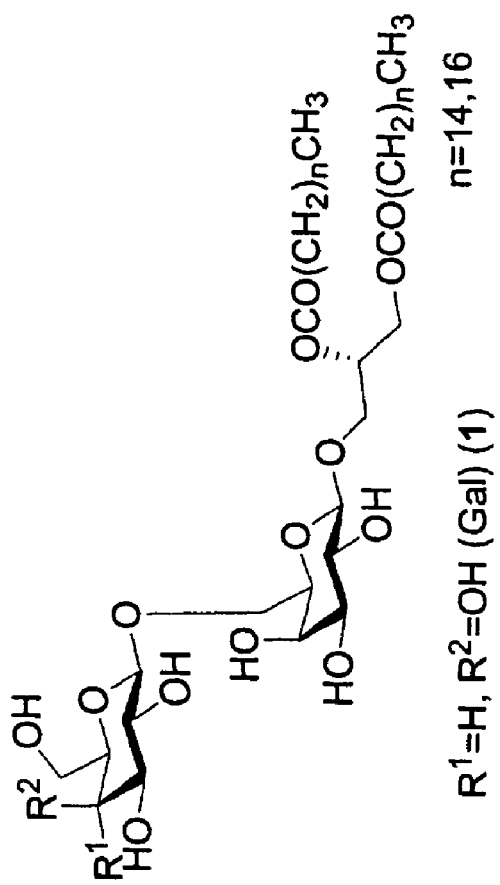
FIG. 1 shows structures of
3-O-[(β-D-Galactopyranosyl)-(1,6)-(β-D-galactopyranosyl)]-1,2-diacyl-O-acyl-sn-glycerol (1) and
3-O-[(β-D-Glucopyranosyl)-(1,6)-(β-D-galactopyranosyl)]-1,2-diacyl-O-acyl-sn-glycerol (2) of the present invention.
Figure 2:
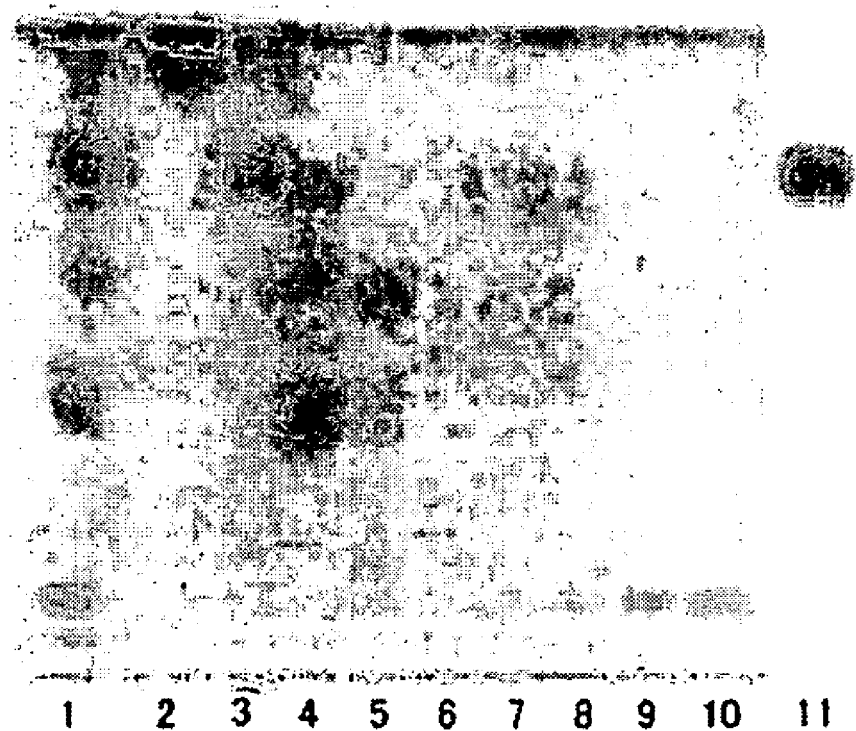
FIG. 2 shows a lipid sample extracted in Example 1, which was developed using thin layer chromatography (TLC) and stained with an orcinol reagent.

FIG. 2 shows that lipid samples were developed using thin layer chromatography (TLC) and stained with an orcinol reagent. Lane 1 shows a lipid fraction extracted from a fungus body prior to purification, lanes 2 to 10 show respective fractions separated by means of the first column chromatography, and lane 11 shows a glycolipid fraction of interest obtained by 3 stages of purification.

3. NMR Analysis

The obtained glycolipid fraction was dissolved in a solution in which DMSO-d6:D2O=98:2, and 1H-NMR was measured at 60° C. No signal of sphingosine was observed, and proton of the glycerol portion was clearly observed. Therefore, it was determined that the fraction was a glycerolipid. There were 2 peaks derived from fatty acids. Most of the fatty acids were saturated, and there were just a few unsaturated fatty acids. Therefore, it was determined that the lipid portion was diacylglycerol (DAG). In the sugar portion, anomeric protons of one glucose and three galactoses, all of which were 1-type, were observed. It seemed that the glucose had a non-reducing terminus and that two of the galactoses had a substituent at position 6. Based on the above-described information, it was thought that skeletons of Galβ-6Galβ-3DAG and Glcβ-6Galβ-3DAG were mixed together. In order to verify the skeleton, whether or not a sugar with a nonreducing terminus bound to position 6 of galactose with a reducing terminus was examined by means of comparison of chemical shift at position 6 using Gal-DAG. Moreover, when measurement was performed in DMSO-d6 100% (not including D2O) and identification of proton of —OH was performed, —OH signal of positions 2, 3 and 4 of galactose with a reducing terminus was observed, but —OH signal of position 6 was not observed. Based on the above-described matters, it was determined that the sugar with the nonreducing terminus bound to position 6.

Figure 3:
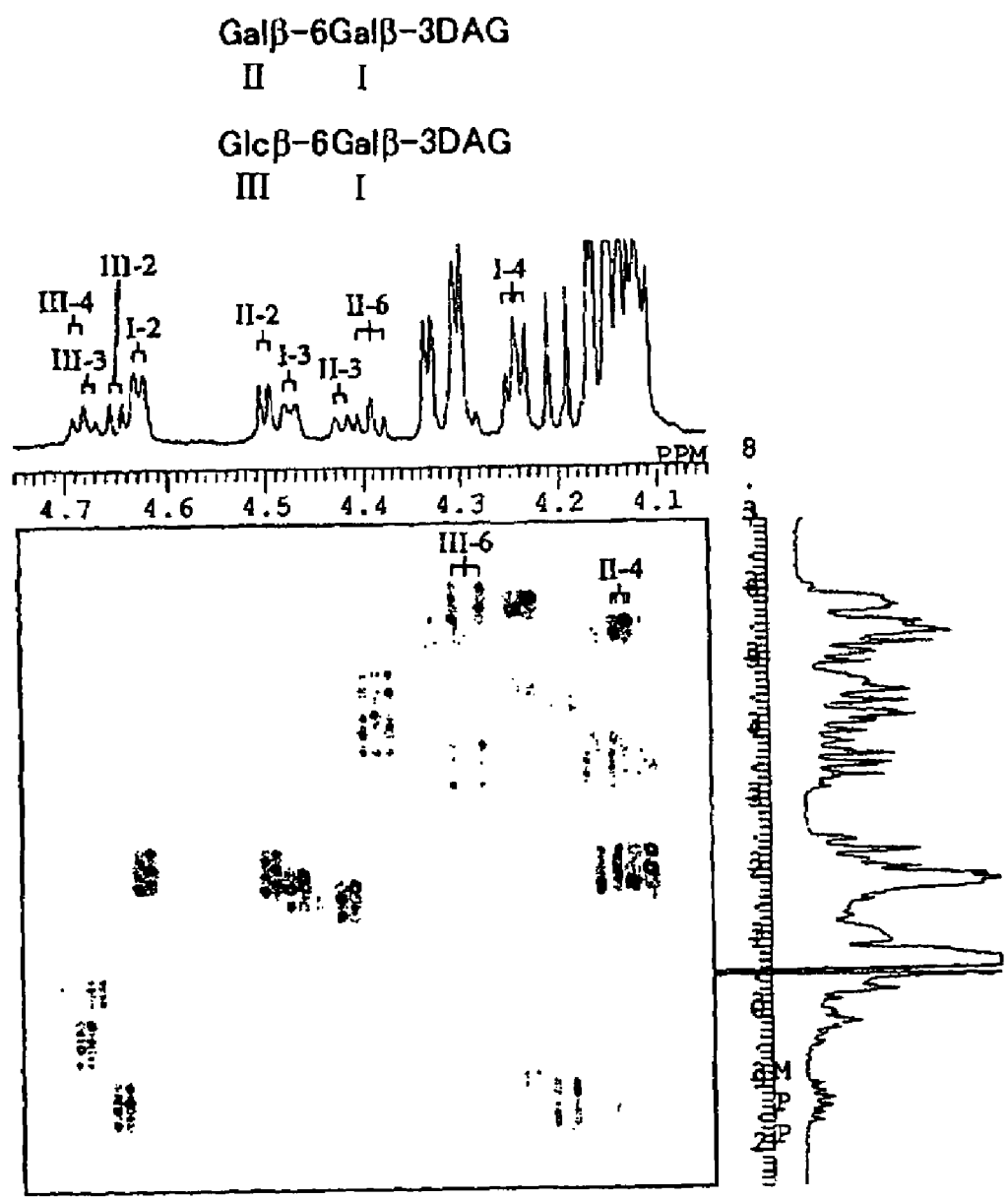
FIG. 3 shows a DQF-COSY spectrum of the lipid fraction obtained in Example 1, which was measured in DMSO-$d_6$ 100%.

FIG. 3 shows DQF-COSY spectrum measured in DMSO-d6 100%, and belongingness of protons of —OH was described therein. Table 1 shows data of belongingness of each proton measured under the following conditions: DMSO-d6:D2O=98:2; 60° C.

TABLE 1

| | δ ppm/($^2$J, and $^3$J in Hz) | |
|---|---|---|
| | Galβ-6Galβ-3DAG (1) | Glcβ-6Galβ-3DAG (2) |
| | sn-glycerol | |
| H-1proR | 4.14 | 4.14 |
| H-1proS | 4.32 | 4.32 |
| H-2 | 5.11 | 5.11 |
| H-3proR | 3.84 | 3.83 |
| H-3proS | 3.63 | 3.64 |
| | -6Galβ1- | |
| H-1 | 4.12 (7.9) | 4.13 (7.9) |
| H-2 | 3.30 | 3.30 |
| H-3 | 3.27 | 3.27 |
| H-4 | 3.68 | 3.68 |
| H-5 | 3.56 | 3.57 |
| H-6proR | 3.62 | 3.63 |
| H-6proS | 3.83 | 3.84 |
| | Galβ1- (for 1) or Glcb1- (for 2) | |
| H-1 | 4.16 (7.0) | 4.20 (7.0) |
| H-2 | 3.30 | 2.97 |
| H-3 | 3.26 | 3.15 |
| H-4 | 3.64 | 3.06 |
| H-5 | 3.33 | 3.11 |
| H-6proR | 3.49 | 3.44 |
| H-6proS | 3.55 | 3.68 |

4. Mass Analysis

Figure 4:
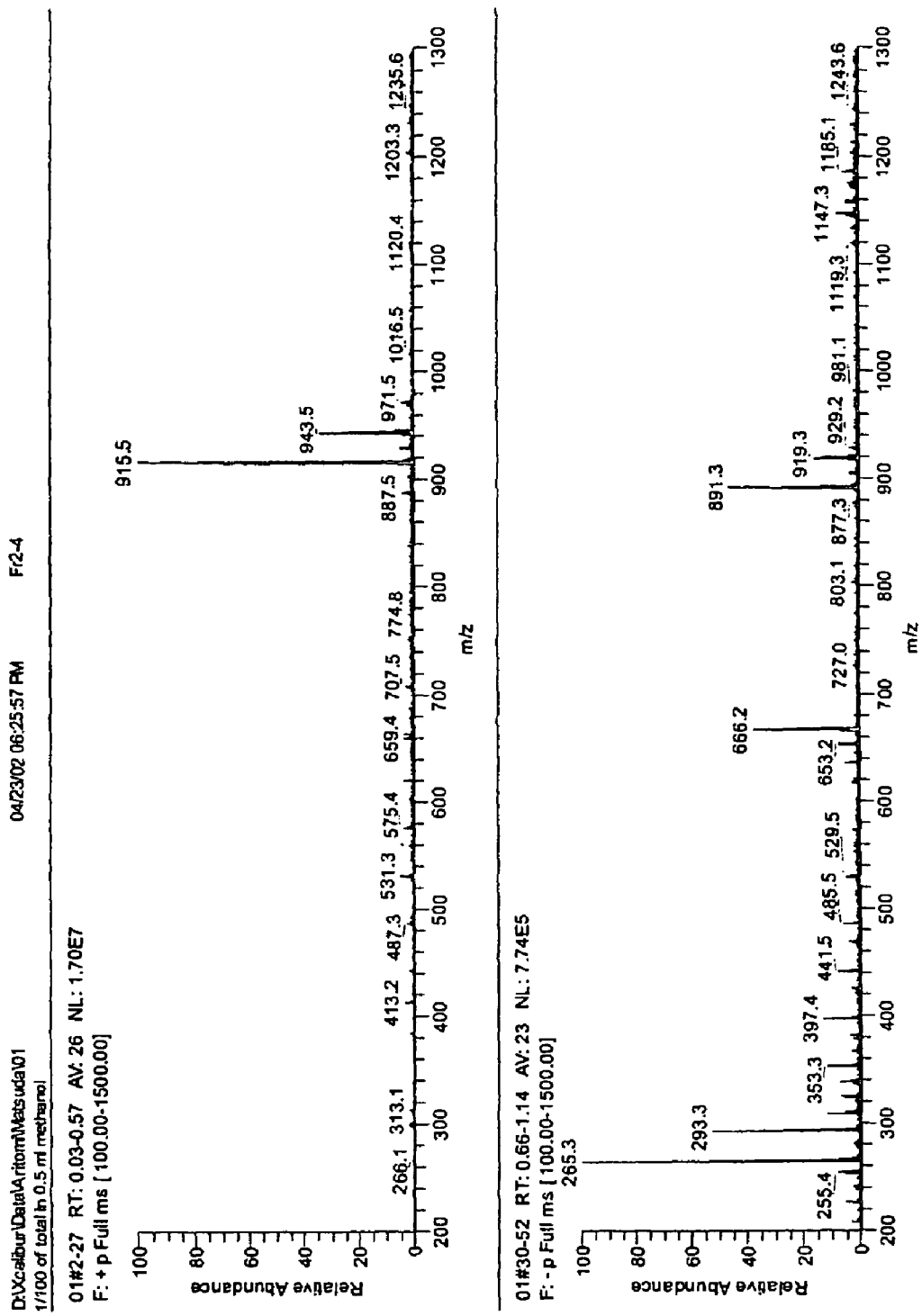
FIG. 4 shows a spectrum chart of the lipid fraction obtained in Example 1 which was obtained by analysis using the ESI-MS measurement.

The obtained lipid fractions were analyzed by ESI-MS measurement. The spectrum chart thereof is shown in FIG. 4. Positive mode was measured under the condition of sodium addition, and molecular ion peaks of m/z 915 (M+23) and 943 (M'+23) were observed. The result was caused by the difference between the compositions of fatty acid, and it was expected that the former was C16:0/16:0 (100%) and the latter was C16:0/18:0 (30%). When these molecular fragments were subjected to MS/MS, a fragment in which fatty acid, sugar portion and glycerol portion were removed from the skeleton of hexose-hexose-diacylglycerol was observed. Thus, the result consistent with this skeleton was obtained. In the case of negative mode, molecular ion peaks of m/z 891 (M−1) and 919 (M'−1) were observed, and in MS/MS measurement thereof, similar consistent result was obtained.

When considering the results of 1H-NMR analysis in combination with the results of mass analysis, it was determined that the structures were those of Galβ-6Galβ-3DAG and Glcβ-6Galβ-3DAG.

5. Settlement of Structures by Data Comparison with Chemically-Synthesized Products In order to settle the structures, the respective skeletons were synthesized stereoselectively and regioselectively by means of chemical synthesis. 1H-NMR measurement was performed under the conditions similar to those for the natural products (DMSO-d6:D2O=98:2; 60° C.), and spectra thereof was analyzed and compared to each other. As a result, the spectra of the synthesized products corresponded to those of the natural products, and thereby the absolute structures were successfully settled.

Table 2 shows data of belongingness of each proton of the natural and synthesized products. The ppm values and coupling constants (J Hz) of the spectra corresponded to each other, and the shapes were also identical.

TABLE 2

| | δ ppm/($^2$J, and $^3$J in Hz) | | | |
|---|---|---|---|---|
| | Galβ-6Galβ-3DAG (1) | | Glcβ-6Galβ-3DAG (2) | |
| | natural | synthesized | natural | synthesized |
| | sn-glycerol | | | |
| H-1proR | 4.14 | 4.14 | 4.14 | 4.13 |
| H-1proS | 4.32 | 4.31 | 4.32 | 4.30 |
| H-2 | 5.11 | 5.11 | 5.11 | 5.10 |
| H-3proR | 3.84 | 3.82 | 3.83 | 3.81 |
| H-3proS | 3.63 | 3.62 | 3.64 | 3.63 |
| | -6Galβ1- | | | |
| H-1 | 4.12 (7.9) | 4.11 (7.5) | 4.13 (7.9) | 4.11 (7.5) |
| H-2 | 3.30 | 3.30 | 3.30 | 3.28 |
| H-3 | 3.27 | 3.27 | 3.27 | |
| H-4 | 3.68 | 3.67 | 3.68 | 3.67 |
| H-5 | 3.56 | 3.56 | 3.57 | 3.56 |
| H-6proR | 3.62 | 3.62 | 3.63 | 3.62 |
| H-6proS | 3.83 | 3.83 | 3.84 | 3.83 |
| | Galβ1- (for 1) or Glcb1- (for 2) | | | |
| H-1 | 4.16 (7.0) | 4.15 (7.0) | 4.20 (7.0) | 4.19 (7.5) |
| H-2 | 3.30 | 3.30 | 2.97 | 2.96 |
| H-3 | 3.26 | 3.26 | 3.15 | 3.14 |
| H-4 | 3.64 | 3.64 | 3.06 | 3.05 |
| H-5 | 3.33 | 3.33 | 3.11 | 3.10 |
| H-6proR | 3.49 | 3.49 | 3.44 | 3.43 |
| H-6proS | 3.55 | 3.54 | 3.68 | 3.65 |

Glyceroglycolipids have been found in many plant bacteria, etc., but a structure having β-type sugar bindings in which 2 sugars have a 1-6 binding has never been reported. The glycolipids represented by the structural formulae 1 and 2 have a novel structure.

Example 2

Figure 5:
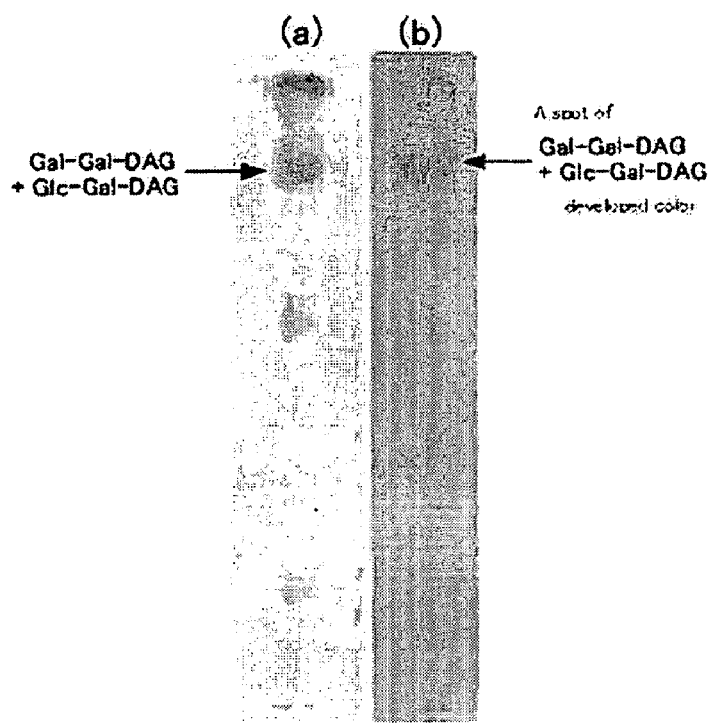
FIG. 5 shows results obtained by: subjecting a lipid fraction of *Mycoplasma pneumoniae* to TLC development; and (a) staining the fraction with an orcinol reagent and (b) detecting a reaction between the fraction and serum from a patient suffering from Guillain-Barre syndrome using the TLC-Immunostaining method. As shown in (b), the spot of glycolipid antigen colored, and this indicates that the patient suffering from Guillain-Barre syndrome has an antibody to the glycolipid antigen.

Antibodies to the Glycolipid Antigens of the Present Invention in a Sample from a Patient Suffering from Nervous Disease An experiment in which lipid fractions of *Mycoplasma pneumoniae* comprising the glycolipid antigens represented by structural formulae 1 and 2 are reacted with serum from a patient suffering from Guillain-Barre syndrome was conducted according to TLC-Immunostaining method. Lipid fractions extracted from *Mycoplasma pneumoniae* were developed on a TLC plate, and serum from a patient suffering from Guillain-Barre syndrome was reacted therewith. The reaction was detected using a mixture of peroxidase-labeled anti-human IgG, IgM and IgA, and visualization was performed using chemical color development. FIG. 5 shows results of TLC development of lipid fractions of *Mycoplasma pneumoniae* ((a): stained with an orcinol reagent; and (b): reaction with serum from a patient suffering from Guillain-Barre syndrome was detected using TLC-Immunostaining method).

As shown in FIG. 5(b), luminescence was found on spots of the glycolipid antigens represented by structural formulae 1 and 2. Therefore, it was proved that the patient suffering from Guillain-Barre syndrome had antibodies to these glycolipid antigens.

This experimental result indicates that the glycolipid antigens represented by structural formulae 1 and 2 and antibodies thereof may be used as a diagnostic marker for a disease caused by *Mycoplasma pneumoniae* infection.

Example 3

2 types of ELISA kits, in which Glcβ-6Galβ-3DAG and Galβ-6Galβ-3DAG prepared by synthesis were used respectively, were prepared, and IgM antibody titers to these antigens in human analytes were measured. As analytes, 40 paired sera from patients suffering from mycoplasma pneumonia were measured in order to examine whether or not the ELISA method is useful as a method for diagnosing mycoplasma pneumonia. 40 sera from healthy individuals were also measured for comparison of scores.

Preparation of antigen plates: 5 μg/mL of Glcβ-6Galβ-3DAG was prepared (methanol: acetonitrile solution). Each 50 μL of this solution was spread on each immunoplate for ELISA (flat bottom). Solvent was removed to prepare plates on which Glcβ-6Galβ-3DAG was immobilized. Plates of Galβ-6Galβ-3DAG were prepared in the same technique.

Protocol of ELISA: Blocking solution was developed in measurement wells (100 μL/well), and incubation was performed at room temperature for 1 hour. After that, washing was applied thereto, each 100 μL of analyte solution to be measured was spread thereon, and incubation was performed at room temperature for 2 hours (double measurement was performed). After that, washing is applied thereto, and subsequently, each 100 μL of solution of peroxidase-labeled IgM antibody was spread thereon, and incubation was performed at room temperature for 2 hours. After that, washing was applied thereto, a TMB solution was added thereto as a coloring substance, and reaction was performed for 15 minutes. After that, the reaction was terminated using 1N aqueous solution of sulfuric acid, and absorbance was measured.

Measurement results: Absorbance was arbitrarily scored based on the standard curve obtained using control, and antibody titers of the analytes were compared to each other. As a result of the ELISA measurement using Glcβ-6Galβ-3DAG, all the scores of the samples from the healthy individuals were 2.5 or lower, and half of the scores were less than 1. On the other hand, all the scores of the sera from the patients suffering from mycoplasma pneumonia were 1 or more, 28% of the scores were 2.5 or lower, and 72% of the scores were higher than 2.5. When the result was represented by ROC curve (sensitivity: false positive rate), the area under the ROC curve was 0.95. It was evaluated that the ability to identify a disease in this measurement was significantly high.

According to the result of the ELISA measurement using Galβ-6Galβ-3DAG, the ability to identify a disease was low, and high scores were detected even in the case of healthy individuals.

Figure 6:
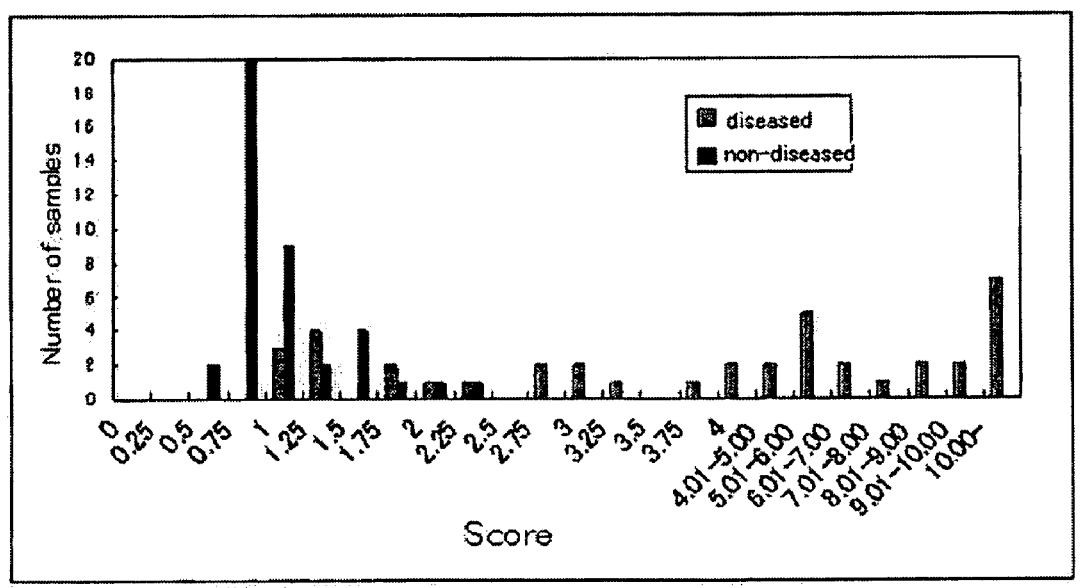
FIG. 6 shows a distribution of scores of disease groups and non-disease groups studied by means of the ELISA method using Glcβ-6Galβ-3DAG in Example 3.
Figure 7:
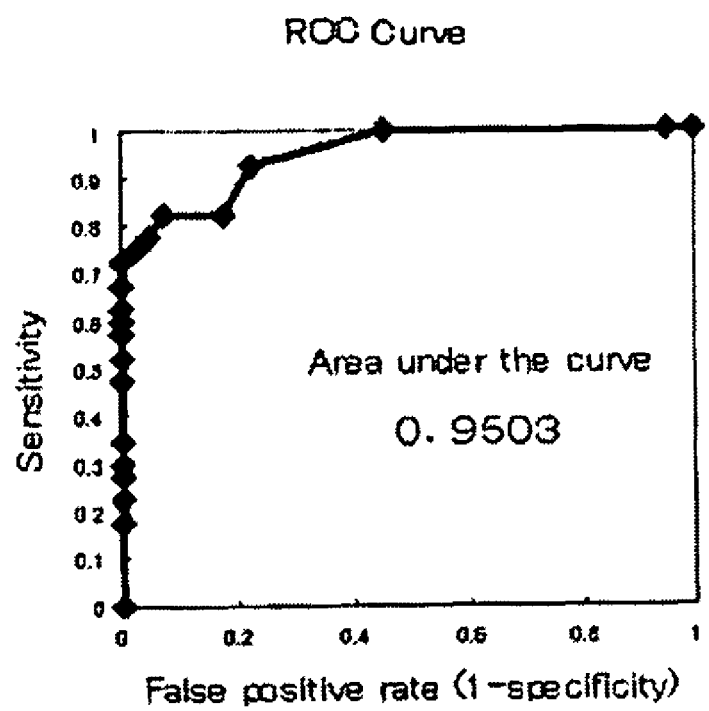
FIG. 7 shows a ROC curve (Receiver Operating Characteristic curve), wherein experimental results obtained by means of the ELISA method using Glcβ-6Galβ-3DAG in Example 3 are represented by values of the ratio between sensitivity and false positive.

FIG. 6 shows results of the ELISA measurement using Glcβ-6Galβ-3DAG, and score distribution of groups having a disease and groups without disease (healthy individuals) is shown. FIG. 7 shows an ROC curve, in which this measurement results are represented by values of the ratio between sensitivity and false positive rate.

The experimental results show that mycoplasma pneumonia, which is caused by *Mycoplasma pneumoniae* infection, can be identified by antibody measurement using Glcβ-6Galβ-3DAG and Galβ-6Galβ-3DAG. In addition, there is a difference between the abilities of the two antigen glycolipids, and there is a possibility that using one of them solely may produce different results. It is considered that use of Glcβ-6Galβ-3DAG is desirable for diagnosing mycoplasma pneumonia.

Example 4

Immunochromatography (1) Preparation of Gold Colloid Solution

A commercially-available solution of gold colloid having the particle diameter of 40 nm manufactured by Biocell Research Laboratories (Cardiff, U.K.) was used without changing its concentration.

(2) Preparation of Solution of Gold Colloid-Labeled Glycolipid Antigen

A glycolipid antigen GlcGL from *Mycoplasma pneumoniae* was used in order to prepare gold colloid label. 1 ml of GlcGL antigen (10 μg/ml) was mixed with 1 ml of the gold colloid solution obtained in (1), and the mixture was allowed to stand at room temperature for 30 minutes to let the antigen bind to the surfaces of gold colloid particles. After that, 10% bovine serum albumin (hereinafter referred to as "BSA") solution was added thereto so that the final concentration of the gold colloid solution became 1%, and remaining surfaces of the gold colloid particles were blocked to prepare a solution of gold colloid-labeled antigen (hereinafter referred to as "gold colloid-labeled antigen"). The solution was centrifuged (8000×G 10 minutes) to precipitate the gold colloid-labeled antigen, and it was washed with 50 mM Tris-HCl buffer (pH 7.4) three times. Supernatant fluid was removed therefrom to obtain the gold colloid-labeled antigen. This gold colloid-labeled antigen was suspended in 50 mM Tris-HCl buffer (pH 7.4) containing 1% saccharose and 0.5% BSA to obtain a solution of gold colloid-labeled antigen.

Figure 8:
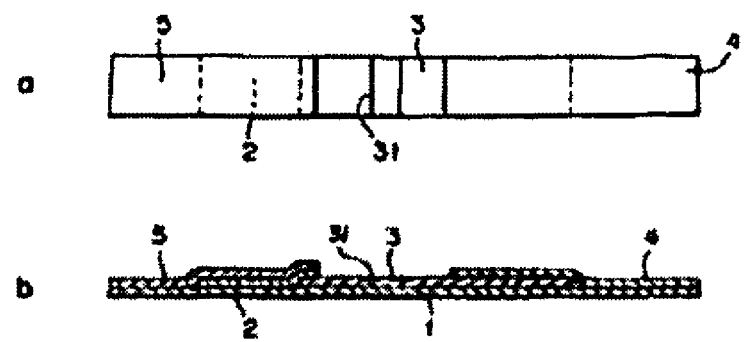
FIG. 8(a) shows a plan view of a test strip of the immunochromato method.
FIG. 8(b) shows a longitudinal sectional view of the test strip of the immunochromato method shown in (a). Reference numerals therein designate things as follows.

(3) Preparation of Test Strip of the Immunochromato Method for the Measurement of Anti-*Mycoplasma Pneumoniae*-Specific Antibody A test strip of the immunochromato method shown in FIG. 8 was prepared according to the following procedures.

(3-1) Capture Site of Complex of Anti-*Mycoplasma pneumoniae*-Specific Antibody and Gold Colloid-Labeled Antigen A strip-shaped nitrocellulose membrane (width: 5 mm, length: 36 mm) was prepared as a membrane carrier 3 for the development of chromatographic medium.

4 μl of solution comprising 2 mg/ml of anti-human IgM antibody was applied in a linear manner to the position of 7.5 mm from the terminus at the starting point side of chromatographic development in the membrane carrier 3. This was dried at room temperature for 3 days, and thus a capture site 31 of complex of anti-*Mycoplasma pneumoniae* antibody and gold colloid-labeled antigen was obtained.

(3-2) Gold Colloid-Labeled Antibody-Impregnated Member

A strip-shaped glass fiber nonwoven fabric (5 mm×15 mm) was impregnated with 40 μl of solution of gold colloid-labeled antigen. This was dried at room temperature to obtain a gold colloid-labeled antibody-impregnated member 2.

(3-3) Preparation of Test Strip of the Immunochromato Method

In addition to the above-described membrane carrier 3 for chromatographic development and the labeled antibody-impregnated member 2, a cotton cloth and a filter paper were prepared as a sample addition member 5 and an absorption member 4, respectively. Using these members, a test strip of the immunochromato method was prepared as shown in FIG. 8.

(4) Test

Sera from patients suffering from pneumonia were diluted with a dilute solution for analytes so that each of them had a predetermined concentration, and thus test samples were obtained. Each of the test samples (40 μl) was dropped on the sample addition member 5 of the test strip obtained in item (3) above using a micropipette to cause chromatographic development. After it was left at room temperature for 10 minutes, the amount of the complex of anti-*Mycoplasma pneumoniae*-specific antibody and gold colloid-labeled antigen captured at the above-described capture site 31 was observed megascopically. The capture amount was judged megascopically according to the color development levels of 1 to 4 (purplish red color), whose increase is proportional to the capture amount, as follows: − (no color development); ± (weak color development); + (clear color development); and ++ (remarkable color development). The results are shown in Table 3.

TABLE 3

| Sample | Results of judgment | | | | |
|---|---|---|---|---|---|
| (Dilution ratio) | 1 | 2 | 4 | 8 | 10 |
| Analyte from patient with pneumonia 1 | ++ | ++ | + | + | ± |
| Analyte from patient with pneumonia 2 | ++ | ++ | + | ± | − |
| Analyte from healthy subject 1 | − | − | − | − | − |
| Analyte from healthy subject 2 | − | − | − | − | − |

Example 5

Preparation of Anti-*Mycoplasma pneumoniae* Glycolipid Polyclonal Antibody 1 ml of fungus body of *Mycoplasma pneumoniae* cultured with 20% goat serum was subjected to 10-fold dilution (10 ml), and 10 ml of Freund's complete adjuvant was added thereto. The mixture was ground at 400 rpm to obtain an emulsion. A goat was immunized subcutaneously with 10 ml of the above-described prepared emulsion, and one month later, 10 ml of the emulsion was used for additional immunization. In addition, the goat was further subjected to additional immunization bimonthly using fungus body of *Mycoplasma pneumoniae* cultured with 20% goat serum. Serum was separated from the goat blood immunized as described above according to the ordinary method. TLC immunostaining was performed using the serum, and the reactivity with the specific antigen glycolipid was confirmed.

TLC Immunostaining:

Operation for the experiment was performed according to the general method. A lipid mixture extracted from the fungus body of *Mycoplasma pneumoniae* and Galβ1-6Galβ-3DAG and Glcβ1-6Galβ-3DAG prepared by chemical synthesis were developed on an HTLC plate, and the obtained goat serum was reacted therewith. The reaction was detected using peroxidase-labeled anti-goat IgG, and the reaction caused by peroxidase was detected by visualization using a Konica immunostaining kit. Results are shown in FIG. 9. The right figure shows the result of immunostaining using the obtained goat serum. The left figure shows the result of orcinol staining of the HTLC plate on which the compounds were developed.

As shown in FIG. 9, color development was recognized on the spots corresponding to Galβ1-6Galβ-3DAG and Glcβ1-6Galβ-3DAG, and thus, it was confirmed that the prepared goat serum has the reactivity therewith.

Example 6

Preparation of Anti-GGL Monoclonal Antibody (1) Preparation of Hybridoma 0.5 ml of emulsion comprising the fungus body of *Mycoplasma pneumoniae* was subcutaneously injected into a 7-week-old female BALB/c mouse. At the second week and third week after the first immunization, 0.5 ml of emulsion prepared using the above-described method was injected subcutaneously and intraperitoneally into the mouse.

Four days after the final immunization, the spleen was removed from the mouse, and a cell suspension was prepared using RPMI1640 medium. $2 \times 10^8$ splenic cells were mixed with mouse myeloma SP2/0 cells ($2 \times 10^7$) in the logarithmic growth phase. After the mixture was centrifuged, to the obtained sediment, 1 ml of 45% polyethylene glycol (PEG4000, manufactured by Wako Pure Chemical Industries, Ltd.) was added with gentle shaking for 1 minute. After that, the mixture was incubated at 37° C. for 2 minutes with shaking. To this mixture. 1 ml of RPMI1640 medium was added for 1 minute, and 8 ml of the medium was further added for 3 minutes.

After the above-described cell mixture was centrifuged, cells were suspended in 50 ml of RPMI1640 medium comprising 10% fetal calf serum (FCS), and it was dividedly poured into four 96-well microplates (100 μl/well). They were cultured in a carbon dioxide incubator (5% carbon dioxide, 37° C.). After 24 hours, the medium was replaced by HAT medium (10% (V/V) FCS medium containing hypoxanthine, aminopterin and thymidine), and the cells were further cultured in the carbon dioxide incubator (5% carbon dioxide, 37° C.). On the fourth day, new HAT medium was added thereto (100 μl/well). On the seventh day, the medium was replaced by HT medium (produced by removing aminopterin from HAT medium), and on the next day, it was replaced by RPMI1640 medium comprising 10% (V/V) FCS. After that, the presence/absence of colony formation was checked.

(2) Selection of Antibody-Producing Hybridoma

Antibody-producing hybridomas were repeatedly cloned by means of limiting dilution. They were screened by ELISA using fungus body of *Mycoplasma pneumoniae* as an antigen to obtain reactive hybridoma G1E6 and M2F8 strains.

(3) Obtainment of Monoclonal Antibody

Subsequently, G1E6 and M2F8 strains were cultured in RPMI1640 medium comprising 10% (V/V) FCS. By collecting culture supernatant thereof, a culture solution comprising a monoclonal antibody was obtained. The monoclonal antibody was purified by ammonium sulfate fractionation, and it was subjected to ELISA (as described below) in which Galβ1-6Galβ-3DAG and Glcβ1-6Galβ-3DAG were used as antigens. The monoclonal antibody reacted with both GalGL and GulGL. The results are shown in FIG. 10.

ELISA Method:

Synthesized Galβ1-6Galβ-3DAG and Glcβ1-6Galβ-3DAG (5 μg/ml each) were prepared using a solvent (methanol: acetonitrile=2:1). Each of the obtained solutions was poured into a 96-well microplate (50 μl/well) and subjected to air drying in a chemical hood, and subsequently subjected to vacuum treatment for 15 hours to prepare an ELISA plate to which antigen glycolipids were attached. ELISA measurement protocol was employed according to the general method. Firstly, 350 μl of blocking solution (obtained by subjecting Blocking One manufactured by Nacalai Tesque, Inc. to 5-fold dilution using water) was dividedly poured into each well and was allowed to stand at 30° C. for 1 hour. After that, it was washed with 0.05% Tween20 in PBS (350 μl/well) five times. Subsequently, 5-fold-diluted 137C culture supernatant (a solution in which Blocking One was subjected to 20-fold dilution using 0.05% Tween20 in PBS was used as a dilute solution) was dividedly poured into each well (100 μl/well) and allowed to stand at 30° C. for 2 hours. After that, it was washed with 0.05% Tween20 in PBS (350 μl/well) five times. Subsequently, a solution of 5000-fold-diluted Goat anti-mouse IgG-HRP [ZYMED Laboratories, cat. #81-6520] or a solution of 5000-fold-diluted Goat-anti-IgM [ZYMED Laboratories, cat. #61-6820] (a solution in which Blocking One was subjected to 20-fold dilution using 0.05% Tween20 in PBS was used as a dilute solution) was dividedly poured into each well (100 μl/well), and it was allowed to stand at 30° C. for 1 hour. After that, it was washed with 0.05% Tween20 in PBS (350 μl/well) five times, and a chromogenic substrate (TMB solution) was dividedly poured into each well (100 μl/well). After it was allowed to stand at 30° C. for 30 minutes, 1N H2SO4 was dividedly poured into each well (50 μl/well) for mixing to terminate color development, and the absorbance (450 nm/620 nm) was measured.

INDUSTRIAL APPLICABILITY

The glyceroglycolipid of the present invention is the main antigen of *Mycoplasma pneumoniae*, and therefore can be a molecular basis for high-sensitively and accurately detecting this microorganism. When utilizing this glycolipid, a method for accurately diagnosing a disease caused by *Mycoplasma pneumoniae* can be developed. The glyceroglycolipid of the present invention can be used as a marker for diagnosing a disease caused by *Mycoplasma pneumoniae*.

The invention claimed is:

1. An isolated compound represented by the following general formula:

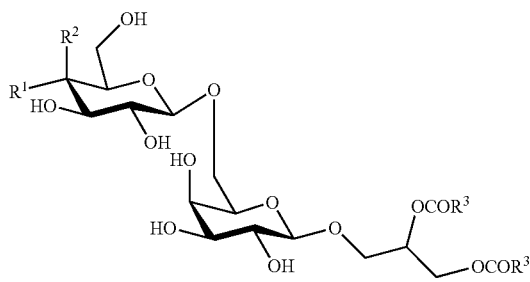

wherein in the formula: when $R^1$=OH, $R^2$=H; when $R^1$=H, $R^2$=OH; and at least one of $R^3$ is —$(CH_2)_{14}CH_3$, and the other $R^3$ is —$(CH_2)_{14}CH_3$ or —$(CH_2)_{16}CH_3$ or a salt thereof.

2. A diagnostic kit for detection of a disease caused by *Mycoplasma pneumoniae*, which comprises the compound according to claim 1 and manufacturer's instructions.

3. The compound according to claim 1, wherein the compound has galactose at the nonreducing terminus.

4. The compound according to claim 1, wherein the compound has glucose at the nonreducing terminus.

5. The diagnostic kit according to claim 2, wherein the compound has galactose at the nonreducing terminus.

6. The diagnostic kit according to claim 2, wherein the compound has glucose at the nonreducing terminus.

7. An isolated compound represented by the following general formula:

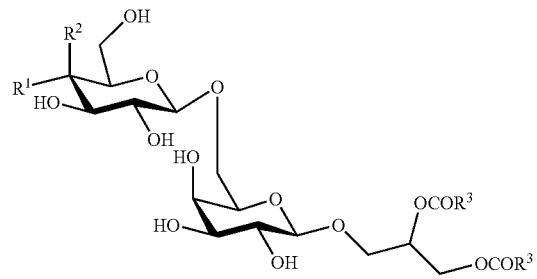

wherein in the formula: when $R^1$=OH, $R^2$=H; when $R^1$=H, $R^2$=OH; and at least one of $R^3$ is —$(CH_2)_{14}CH_3$, and the other $R^3$ is —$(CH_2)_{14}CH_3$ or —$(CH_2)_{16}CH_3$ or a salt thereof, wherein said compound is an isolated natural compound derived from *Mycoplasma pneumoniae*.

8. A chemically synthesized compound represented by the following general formula:

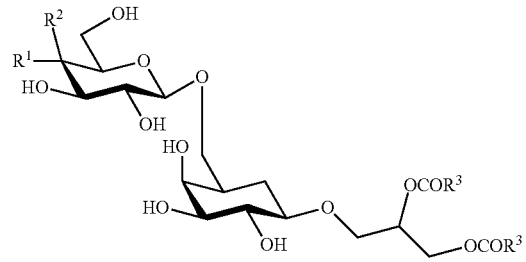

wherein in the formula: when $R^1$=OH, $R^2$=H; when $R^1$=H, $R^2$=OH; and at least one of $R^3$ is —$(CH_2)_{14}CH_3$, and the other $R^3$ is —$(CH_2)_{14}CH_3$ or —$(CH_2)_{16}CH_3$ or a salt thereof.

* * * * *